United States Patent
Watanabe et al.

(10) Patent No.: US 12,296,033 B2
(45) Date of Patent: May 13, 2025

(54) WATER-TYPE OR OIL-IN-WATER-TYPE COSMETIC PRODUCT

(71) Applicant: Shiseido Company, Ltd., Tokyo (JP)

(72) Inventors: Yurika Watanabe, Tokyo (JP); Takashi Ishida, Tokyo (JP); Kazuhiro Yamaguchi, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 835 days.

(21) Appl. No.: 17/311,278

(22) PCT Filed: Nov. 18, 2019

(86) PCT No.: PCT/JP2019/045024
§ 371 (c)(1),
(2) Date: Jun. 4, 2021

(87) PCT Pub. No.: WO2020/116137
PCT Pub. Date: Jun. 11, 2020

(65) Prior Publication Data
US 2022/0015996 A1    Jan. 20, 2022

(30) Foreign Application Priority Data
Dec. 7, 2018    (JP) .................. 2018-229841

(51) Int. Cl.
*A61K 8/06* (2006.01)
*A61K 8/25* (2006.01)
*A61Q 17/04* (2006.01)

(52) U.S. Cl.
CPC ............ *A61K 8/062* (2013.01); *A61K 8/25* (2013.01); *A61Q 17/04* (2013.01); *A61K 2800/412* (2013.01); *A61K 2800/48* (2013.01)

(58) Field of Classification Search
CPC .... A61K 8/062; A61K 8/25; A61K 2800/412; A61K 2800/48; A61K 8/0279; A61K 8/025; A61Q 17/04
See application file for complete search history.

(56) References Cited

U.S. PATENT DOCUMENTS

| | | | |
|---|---|---|---|
| 2005/0074474 A1* | 4/2005 | Sako | A61Q 19/00 424/59 |
| 2010/0247914 A1 | 9/2010 | Enomoto et al. | |
| 2016/0143831 A1 | 5/2016 | Brock et al. | |

FOREIGN PATENT DOCUMENTS

| | | | | |
|---|---|---|---|---|
| EP | 2 774 598 A1 | 9/2014 | | |
| EP | 3 449 896 A1 | 3/2019 | | |
| JP | 08-067867 A | 3/1996 | | |
| JP | 2005-060263 A | 3/2005 | | |
| JP | 2009-137806 A | 6/2009 | | |
| JP | 2011-020966 A | 2/2011 | | |
| JP | 2016-523938 A | 8/2016 | | |
| JP | 2018-070556 A | 5/2018 | | |
| WO | WO-2011/111828 A1 | 9/2011 | | |
| WO | WO-2012139246 A2 * | 10/2012 | ............. | A61K 47/02 |

* cited by examiner

*Primary Examiner* — Robert A Wax
*Assistant Examiner* — Quanglong N Truong
(74) *Attorney, Agent, or Firm* — Foley & Lardner LLP

(57) ABSTRACT

A water-type or oil-in-water type cosmetic provided with a watery feeling in use and high ultraviolet protection ability. The water-type or oil-in-water-type cosmetic according to the present invention is characterized by containing (A) a porous spherical powder having an average particle size of 1 to 4 μm and an oil absorption rate of 160 ml/100 g or lower; and (B) an ultraviolet absorption agent.

7 Claims, No Drawings

WATER-TYPE OR OIL-IN-WATER-TYPE COSMETIC PRODUCT

CROSS-REFERENCE TO RELATED APPLICATIONS

This application is the U.S. National Stage of PCT/JP2019/045024, filed Nov. 18, 2019, which claims priority to JP 2018-229841, filed Dec. 7, 2018.

TECHNICAL FIELD

The present invention relates to a water-type or an oil-in-water-type cosmetic. More specifically, the present invention relates to a water-type or oil-in-water-type cosmetic that, by blending in a porous spherical powder having a prescribed average particle size and oil absorption rate, achieves high ultraviolet protection ability even without blending in a large amount of ultraviolet absorbing agents.

BACKGROUND ART

Water-type or oil-in-water-type cosmetics allow a fresh and watery feel to be obtained when applied to skin, and thus are widely used as base agents for external skin-care preparations, such as skin cosmetics, that are directly applied to the skin. In particular, since the protection of the skin from ultraviolet rays has become a matter of daily routine in skin care and body care, the importance of using a water-type or an oil-in-water-type cosmetic as the base agent in such a UV-care cosmetic is increasing.

The ultraviolet absorption agents that are blended into common sunscreen cosmetics are often oil-soluble for reasons such as ultraviolet absorption ability, ease of handling and cost. However, oil-soluble ultraviolet absorption agents cause stickiness, and if a large amount is blended into a water-type or oil-in-water-type cosmetic, the refreshing and watery feel may be lost. For this reason, it is difficult to blend a large amount of an oil-soluble ultraviolet absorption agent into a water-type or an oil-in-water-type cosmetic.

Therefore, for the purpose of maintaining the wateriness of water-type or oil-in-water-type cosmetics, water-soluble ultraviolet absorption agents are blended instead of blending large amounts of oil-soluble ultraviolet absorption agents. However, in general, since water-soluble ultraviolet absorption agents have inferior ultraviolet protection ability in comparison with those that are oil-soluble, it is difficult the achieve sufficient ultraviolet protection ability even by blending in a large amount of a water-soluble ultraviolet absorption agent. Additionally, when a water-soluble ultraviolet absorption agent is blended, there is a problem in that the safety of the cosmetic is lowered due to the influence of salts (neutralizing salts) that are blended therewith. For this reason, it is preferable to avoid blending in a large amount of a water-soluble ultraviolet absorption agent.

Due to these circumstances, various attempts have been made to improve the ultraviolet protection ability in water-type or oil-in-water-type cosmetics.

For example, Patent Document 1 proposes to improve the ultraviolet protection ability by blending in one or more types of hydrophilic non-ionic surfactants selected from among PEG glyceryl fatty acid ester-based surfactants, hydrogenated castor oil-based surfactants and PEG-PPG alkyl ether-based surfactants, thereby allowing water-soluble ultraviolet absorption agents to be blended.

Additionally, Patent Document 2 proposes an oil-in-water emulsion sunscreen cosmetic in which a large amount of an ultraviolet absorption agent can be blended without reducing the stability and the feeling in use, by blending a specific organosiloxane derivative, polyethylene glycol stearate and a higher alcohol at a specified ratio.

However, in order to fundamentally improve the influence that ultraviolet absorption agents have on such properties as the stability of cosmetics, it is preferable to keep the blended amount of ultraviolet absorption agents themselves small. Furthermore, in recent years, the burden that ultraviolet absorption agents pose on the environment has been recognized as a problem, and a technology that achieves higher ultraviolet protection ability with less ultraviolet absorption agent has become necessary.

RELATED ART

Patent Documents

Patent Document 1: JP 2008-162930 A
Patent Document 2: JP 2013-121947 A

SUMMARY OF THE INVENTION

Problem to be Solved by the Invention

An objective of the present invention is to provide a water-type or an oil-in-water-type cosmetic provided with a watery feeling in use and high ultraviolet protection ability.

Means for Solving the Problem

As a result of performing diligent research towards solving the above-mentioned problem, the present inventors discovered that the ultraviolet absorption ability can be increased by blending a porous spherical powder having a prescribed particle size and oil absorption rate, thereby completing the present invention.

In other words, the present invention is an invention that fundamentally differs from conventional methods in which the ultraviolet protection effects are raised by simply increasing the blended amount of ultraviolet absorption agents, and is based on the discovery that a porous spherical powder having a prescribed average particle size and oil absorption rate functions as an improver or a booster of ultraviolet protection ability.

Therefore, the present invention provides a water-type or an oil-in-water-type cosmetic containing:

(A) a porous spherical powder having an average particle size of 1 to 4 μm and an oil absorption rate of 160 ml/100 g or lower; and
(B) an ultraviolet absorption agent.

Effects of the Invention

Due to the above-mentioned features, the present invention can obtain high ultraviolet protection effects even without blending a large amount of ultraviolet absorption agents. For this reason, sufficient ultraviolet protection effects can be obtained with a small amount of an ultraviolet absorption agent, without sacrificing the watery feeling in use that is originally possessed by water-type or oil-in-water-type cosmetics.

MODES FOR CARRYING OUT THE INVENTION

As mentioned above, the water-type or oil-in-water type cosmetic of the present invention is characterized by containing (A) a porous spherical powder and (B) an ultraviolet absorption agent. Hereinafter, the respective components constituting the cosmetic of the present invention will be explained in detail.

<(A) Porous Spherical Powder>

The (A) porous spherical powder (hereinafter sometimes referred to simply as "component (A)") blended into the cosmetic according to the present invention has a prescribed average particle size and oil absorption rate.

The average particle size of the (A) porous spherical powder is 1 to 4 μm, more preferably 1.5 to 4 μm. If the average particle size is smaller than 1 μm, then there is a tendency for the ease of handling to become worse. If the average particle size exceeds 4 μm, then high ultraviolet protection ability increase effects cannot be obtained, in addition to which there is a tendency for graininess to occur, thereby making the texture worse.

The average particle size in the present invention is a value obtained by adding 0.05 g of a powder to 20 g of an ethanol solvent, then using an ultrasonic homogenizer (US-150T; manufactured by Nissei Corp.) to perform ultrasonic dispersion for one minute, and using a laser diffraction/scattering-type particle size distribution measurement device (MT3300EX II; manufactured by MicrotracBEL Corp.) to measure the volume-based average particle size (D50).

The oil absorption rate of the (A) porous spherical powder, in terms of the oil absorption rate measured in accordance with JIS K5101-13-2 (boiled linseed oil method), is 160 ml/100 g or lower, more preferably 50 to 160 ml/100 g, and even more preferably 60 to 160 ml/100 g. If the oil absorption rate is within the above-mentioned ranges, then the ultraviolet protection effects can be sufficiently increased.

The shape of the (A) porous spherical powder is spherical, and in particular, preferably perfectly spherical. The closer the shape of component (A) is to perfectly spherical, the more uniform the thickness of a coating film of the cosmetic that can be formed on skin, thereby allowing high ultraviolet protection ability increase effects to be achieved.

For the purposes of the present invention, "perfectly spherical" refers to a shape that is substantially perfectly circular when viewed as a projection from any direction, wherein the minimum value of the particle size is at least 80%, more preferably at least 90%, of the maximum value.

The material constituting the (A) porous spherical powder is not particularly limited. Examples include silica (silicic anhydride), cellulose and the like, among which silica is preferable.

Examples of commercially available silica powder products that can be used as the (A) porous spherical powder include Godd Ball E-6C, Godd Ball B-6C (both by Suzuki Yushi Industrial Co., Ltd.), Silica Microbead P-500 (JGC C&C), Sunsphere L-31 (AGC Si-Tech Co., Ltd.) and the like.

The (A) porous spherical powder may be used as a single type alone or as a combination of two or more types. The blended amount of component (A) is preferably 1% to 5% by mass, more preferably 2% to 4% by mass relative to the total amount of the water-type or the oil-in-water-type cosmetic. If the blended amount of component (A) is less than 1% by mass, then there is a tendency to not be able to obtain sufficient ultraviolet protection ability increase effects due to component (A). If the blended amount of component (A) exceeds 5% by mass, then there are cases in which the texture becomes worse.

<(B) Ultraviolet Absorption Agent>

As the (B) ultraviolet absorption agent (hereinafter sometimes referred to simply as "component (B)") blended into the cosmetic according to the present invention, a water-soluble ultraviolet absorption agent and/or an oil-soluble ultraviolet absorption agent that is normally blended into sunscreen cosmetics may be used.

Examples of water-soluble ultraviolet absorption agents include phenylbenzimidazole sulfonic acid salts, hydroxymethoxybenzophenone sulfonic acid salts, 4-(2-β-glucopyranosiloxy)propoxy-2-hydroxybenzophenone, phenylene-1,4-bis(2-benzimidazyl)-3,3'-5,5'-tetrasulfonic acid bis-sodium salts and terephthalylidene dichamphor sulfonic acid.

Examples of oil-soluble ultraviolet absorption agents include 2-ethylhexyl-p-methoxycinnamate, 4-tert-4'-methoxydibenzoylmethane, octocrylene, 2,4-bis-[{4-(2-ethylhexyloxy)-2-hydroxy}-phenyl]-6-(4-methoxyphenyl)-1,3,5-triazine, methylene bis-benzotriazolyl tetramethylbutylphenol, 2,4,6-tris[4-(2-ethylhexyloxycarbonyl)anilino]1,3,5-triazine, diethylamino hydroxybenzoyl hexyl benzoate, oxybenzone and dihydroxydimethoxybenzophenone.

Component (B) may be used as a single type alone or as a combination of two or more types. In particular, even higher ultraviolet protection ability can be achieved by using a combination of one or more types of both a water-soluble ultraviolet absorption agent and an oil-soluble ultraviolet absorption agent.

The blended amount of component (B) is preferably 6% to 40% by mass, more preferably 8% to 35% by mass and even more preferably 10% to 30% by mass relative to the total amount of the water-type or the oil-in-water-type cosmetic. If the blended amount of component (B) is less than 6% by mass, then there is a tendency to not be able to obtain sufficient ultraviolet protection effects. If the blended amount of component (B) exceeds 40% by mass, then the conditions are not favorable in that a commensurate increase in ultraviolet protection effects cannot be expected and the stability becomes worse.

Aside from the above-mentioned essential ingredients, components that are normally used in cosmetics may be appropriately blended into the water-type or the oil-in-water-type cosmetic of the present invention as needed. Examples of such components include oils, water, alcohols, surfactants, oil-based active agents, water-soluble active agents, thickeners, humectants, ultraviolet scattering agents, antioxidants and the like.

<Thickener>

In particular, by blending in a thickener, a coating film of the cosmetic having a sufficient thickness can be formed on the skin, and even higher ultraviolet protection ability increase effects can be achieved.

The thickener is not particularly limited as long as it is used in cosmetic products. For example, various types of hydrophilic thickeners such as natural water-soluble polymers, semi-synthetic water-soluble polymers and synthetic water-soluble polymers are preferable.

Examples of natural water-soluble polymers include plant-based polymers such as gum arabic, tragacanth gum, galactan, guar gum, carob gum, karaya gum, carrageenan, pectin, agar, quince seed (marmelo), algecolloid (Phaeophyceae extract), starch (rice, corn, potato, wheat) and glycyrrhizic acid; microbe-based polymers such as xanthan gum, dextran, succinoglycan and pullulan; and animal-based polymers such as collagen, casein, albumin and gelatin.

Examples of semi-synthetic water-soluble polymers include starch-based polymers such as carboxymethyl starch and methylhydroxypropyl starch; cellulose-based polymers such as methyl cellulose, nitrocellulose, ethyl cellulose, methyl hydroxypropyl cellulose, hydroxyethyl cellulose, sodium cellulose sulfate, hydroxypropyl cellulose, sodium carboxymethyl cellulose (CMC), crystalline cellulose and cellulose powder; and alginic acid-based polymers such as sodium alginate and propylene glycol esters of alginic acid.

Examples of synthetic water-soluble polymers include vinyl-based polymers such as polyvinyl alcohol, polyvinyl methyl ether, polyvinyl pyrrolidone and carboxyvinyl polymers (carbomers); polyoxyethylene-based polymers such as polyethylene glycol (molecular weight 1500, 4000, 6000); polyoxyethylene/polyoxypropylene copolymers; acryl-based polymers such as sodium polyacrylate, poly ethyl acrylate, polyacrylamide and acrylic acid/alkyl methacrylate copolymers (e.g., (acrylates/alkyl acrylate (C10-30)) crosspolymer); and polyethylene imine and cationic polymers.

Among the thickeners, acryl-based polymers, xanthan gum, alkyl-modified cellulose and the like are particularly preferable, and it is more preferable to blend a combination of two or more types thereof.

When blending in a thickener, the amount should be 0.01% to 5% by mass, more preferably 0.1% to 3% by mass relative to the total amount of the water-type or oil-in-water-type cosmetic. If the blended amount of the thickener is less than 0.01% by mass, then there are cases in which sufficient thickener effects cannot be obtained. If more than 5% by mass is blended, then there are cases in which there is a feeling of heaviness at the time of application.

The water-type or oil-in-water-type cosmetic of the present invention may be produced in accordance with conventionally used methods, and aside from a sunscreen cream, a sunscreen milky lotion, a sunscreen lotion or the like, may be used as a toner or the like provided with sunscreen effects.

As mentioned above, the present invention is based on the discovery that a porous spherical powder having a prescribed average particle size and oil absorption rate functions as an improver or a booster of ultraviolet protection ability.

Therefore, the present invention includes, as another embodiment, a method for increasing the ultraviolet protection ability of a water-type or oil-in-water type cosmetic containing (B) an ultraviolet absorption agent by blending in (A) a porous spherical powder.

EXAMPLES

Hereinafter, the present invention will be explained in further detail by providing specific examples. However, the present invention is not limited to the examples below. Additionally, the blended amounts in the following examples and the like are indicated in percentage by mass where not particularly indicated otherwise. Before specifically explaining each example, the evaluation method that was used will be explained.

<Measurement of Absorbance Integral (Abs) Value>

Cosmetics (samples) according to each example were dripped, at a rate of 2 mg/cm², onto measurement plates (S plates) (5×5 cm V-groove PMMA plates, SPFMASTER-PA01), applied by finger for 60 seconds, and dried for 15 minutes to form coating films, the absorbances of which were measured using a Hitachi U-3500 self-recording spectrophotometer. The absorbances (Abs) were computed, with uncoated plates as the control, by using the following formula, to determine absorbance integral values by summing the measurement values at 280 nm to 400 nm.

$Abs = -\log(T/T_0)$

T: transmittance of sample, To: transmittance of uncoated plate

From the absorbance integral values of the samples that were determined, the rate of increase in the ultraviolet protection ability, relative to a sample in which a powder was not blended (Comparative Example 1), was computed by the equation below.

[Ultraviolet protection ability increase rate (%)]= [Absorbance integral value of sample]/[Absorbance integral value of Comparative Example 1]×100

The computed ultraviolet protection ability increase rates were assessed in accordance with the evaluation scoring criteria indicated below.

Evaluation Criteria
A: Rate of increase in ultraviolet protection ability was 170% or higher
B: Rate of increase in ultraviolet protection ability was 140% to 170%
C: Rate of increase in ultraviolet protection ability was 105% to 140%
D: Rate of increase in ultraviolet protection ability was lower than 105%

<Texture>

Each sample of the examples and comparative examples was actually used by ten expert panelists and evaluated for texture (lack of stickiness, wateriness). Each of the panelists was asked to perform a five-level organoleptic evaluation in accordance with the evaluation scoring criteria indicated below, and assessments were made by the total scores thereof based on the evaluation criteria indicated below.

Evaluation Scoring Criteria
5: Very good
4: Good
3: Normal
2: Poor
1: Very poor

Evaluation Criteria
A: Total score was 40 or higher
B: Total score was 30 to 39
C: Total score was 20 to 29
D: Total score was 19 or lower <Stability (Rolling Test)>

A cylindrical container was filled with each sample of the examples and comparative examples, a rolling test was performed by rolling the container for 4 hours at a speed of 45 rpm at room temperature, and the degree of aggregation of the powder was observed by eye.

Evaluation Criteria
A: Aggregation of the powder was not observed
B: Aggregation of the powder was observed, but the sample returned to a homogeneous state after stirring
C: Aggregation of the powder was observed, and the sample did not become homogenous even after stirring Examples 1 to 4 and Comparative Examples 1 to 17

Oil-in-water cosmetics having the compositions indicated in Table 1a and Table 1b below were prepared by adding the water phase, obtained by mixing the water phase components with the powder components etc., to the oil phase, obtained by melting and mixing the oil phase components, then emulsifying the mixture by a stirring process. In accordance with the above-mentioned evaluation methods, the absorbance (Abs) integral values were measured, and the ultraviolet protection ability increase effects, the texture and the stability were evaluated.

TABLE 1a

| | | Ex 1 | Ex 2 | Ex 3 | Ex 4 | Comp Ex 1 | Comp Ex 2 | Comp Ex 3 | Comp Ex 4 | Comp Ex 5 | Comp Ex 6 | Comp Ex 7 |
|---|---|---|---|---|---|---|---|---|---|---|---|---|
| Ion-exchanged water | | 61.97 | 61.97 | 61.97 | 61.97 | 64.97 | 61.97 | 61.97 | 61.94 | 61.94 | 61.94 | 61.94 |
| Alcohol | | 10 | 10 | 10 | 10 | 10 | 10 | 10 | 10 | 10 | 10 | 10 |
| Glycerin | | 1 | 1 | 1 | 1 | 1 | 1 | 1 | 1 | 1 | 1 | 1 |
| BG | | 5 | 5 | 5 | 5 | 5 | 5 | 5 | 5 | 5 | 5 | 5 |
| (Acrylates/alkyl acrylate ($C_{10-30}$) crosspolymer *1 | | 0.1 | 0.1 | 0.1 | 0.1 | 0.1 | 0.1 | 0.1 | 0.1 | 0.1 | 0.1 | 0.1 |
| Carbomer *2 | | 0.1 | 0.1 | 0.1 | 0.1 | 0.1 | 0.1 | 0.1 | 0.1 | 0.1 | 0.1 | 0.1 |
| Xanthan gum *3 | | 0.06 | 0.06 | 0.06 | 0.06 | 0.06 | 0.06 | 0.06 | 0.06 | 0.06 | 0.06 | 0.06 |
| PEG-60 glyceryl isostearate *4 | | 0.27 | 0.27 | 0.27 | 0.27 | 0.27 | 0.27 | 0.27 | 0.3 | 0.3 | 0.3 | 0.3 |
| PEG/PPG-19/19 dimethicone *5 | | 1.5 | 1.5 | 1.5 | 1.5 | 1.5 | 1.5 | 1.5 | 1.5 | 1.5 | 1.5 | 1.5 |
| Triethanolamine | | 0.3 | 0.3 | 0.3 | 0.3 | 0.3 | 0.3 | 0.3 | 0.3 | 0.3 | 0.3 | 0.3 |
| PPG-17 *6 | | 1 | 1 | 1 | 1 | 1 | 1 | 1 | 1 | 1 | 1 | 1 |
| Oxybenzone-3 | | 2 | 2 | 2 | 2 | 2 | 2 | 2 | 2 | 2 | 2 | 2 |
| bis-Ethylhexyloxyphenol methoxyphenyl triazine | | 2 | 2 | 2 | 2 | 2 | 2 | 2 | 2 | 2 | 2 | 2 |
| Ethylhexyl methoxycinnamate | | 7 | 7 | 7 | 7 | 7 | 7 | 7 | 7 | 7 | 7 | 7 |
| Dimethicone *7 | | 3 | 3 | 3 | 3 | 3 | 3 | 3 | 3 | 3 | 3 | 3 |
| Hydrogenated polyisobutene | | 1.5 | 1.5 | 1.5 | 1.5 | 1.5 | 1.5 | 1.5 | 1.5 | 1.5 | 1.5 | 1.5 |
| EDTA-2Na·$2H_2O$ | | 0.2 | 0.2 | 0.2 | 0.2 | 0.2 | 0.2 | 0.2 | 0.2 | 0.2 | 0.2 | 0.2 |
| Powder | Silica A | 3 | — | — | — | — | — | — | — | — | — | — |
| | Silica B | — | 3 | — | — | — | — | — | — | — | — | — |
| | Silica C | — | — | 3 | — | — | — | — | — | — | — | — |
| | Silica D | — | — | — | 3 | — | — | — | — | — | — | — |
| | Silica E | — | — | — | — | — | 3 | — | — | — | — | — |
| | Silica F | — | — | — | — | — | — | 3 | — | — | — | — |
| | Silica G | — | — | — | — | — | — | — | 3 | — | — | — |
| | Silica H | — | — | — | — | — | — | — | — | 3 | — | — |
| | Silica I | — | — | — | — | — | — | — | — | — | 3 | — |
| | Silica J | — | — | — | — | — | — | — | — | — | — | 3 |
| Total | | 100 | 100 | 100 | 100 | 100 | 100 | 100 | 100 | 100 | 100 | 100 |
| Powder properties | Shape | sphere | sphere | sphere | sphere | — | sphere | sphere | sphere | sphere | sphere | — |
| | Avg. particle size (μm) | 1.7 | 3.7 | 3.8 | 3.9 | — | 0.58 | 3.8 | 4.1 | 4.3 | 4.5 | 4.6 |
| | Oil absorption rate (mL/100 g) | 60 | 120 | 150 | 140 | — | — | 30 | 100 | 150 | 400 | 300 |
| | Porous/non-porous | porous | porous | porous | porous | — | porous | non-porous | porous | porous | porous | — |
| Absorption integral value | | 70 | 65.2 | 57.2 | 63.2 | 39.4 | 50.6 | 51.2 | 45.6 | 49.3 | 40.5 | 42.2 |
| Ultraviolet protection ability increase rate (%) | | 178 | 165 | 145 | 160 | 100 | 128 | 130 | 116 | 125 | 103 | 107 |
| Ultraviolet protection ability increase effect | | A | B | B | B | D | C | C | C | C | D | C |
| Texture | | B | B | B | A | B | B | B | B | B | B | B |
| Stability (rolling test) | | A | A | A | A | A | A | A | A | A | A | A |

TABLE 1b

| | Comp Ex 8 | Comp Ex 9 | Comp Ex 10 | Comp Ex 11 | Comp Ex 12 | Comp Ex 13 | Comp Ex 14 | Comp Ex 15 | Comp Ex 16 | Comp Ex 17 |
|---|---|---|---|---|---|---|---|---|---|---|
| Ion-exchanged water | 61.94 | 61.94 | 61.94 | 61.94 | 61.94 | 61.94 | 61.94 | 61.94 | 61.94 | 61.94 |
| Alcohol | 10 | 10 | 10 | 10 | 10 | 10 | 10 | 10 | 10 | 10 |
| Glycerin | 1 | 1 | 1 | 1 | 1 | 1 | 1 | 1 | 1 | 1 |
| BG | 5 | 5 | 5 | 5 | 5 | 5 | 5 | 5 | 5 | 5 |
| (Acrylates/alkyl acrylate ($C_{10-30}$) crosspolymer *1 | 0.1 | 0.1 | 0.1 | 0.1 | 0.1 | 0.1 | 0.1 | 0.1 | 0.1 | 0.1 |
| Carbomer *2 | 0.1 | 0.1 | 0.1 | 0.1 | 0.1 | 0.1 | 0.1 | 0.1 | 0.1 | 0.1 |
| Xanthan gum *3 | 0.06 | 0.06 | 0.06 | 0.06 | 0.06 | 0.06 | 0.06 | 0.06 | 0.06 | 0.06 |
| PEG-60 glyceryl isostearate *4 | 0.3 | 0.3 | 0.3 | 0.3 | 0.3 | 0.3 | 0.3 | 0.3 | 0.3 | 0.3 |
| PEG/PPG-19/19 dimethicone *5 | 1.5 | 1.5 | 1.5 | 1.5 | 1.5 | 1.5 | 1.5 | 1.5 | 1.5 | 1.5 |
| Triethanolamine | 0.3 | 0.3 | 0.3 | 0.3 | 0.3 | 0.3 | 0.3 | 0.3 | 0.3 | 0.3 |
| PPG-17 *6 | 1 | 1 | 1 | 1 | 1 | 1 | 1 | 1 | 1 | 1 |

TABLE 1b-continued

|  |  | Comp Ex 8 | Comp Ex 9 | Comp Ex 10 | Comp Ex 11 | Comp Ex 12 | Comp Ex 13 | Comp Ex 14 | Comp Ex 15 | Comp Ex 16 | Comp Ex 17 |
|---|---|---|---|---|---|---|---|---|---|---|---|
| Oxybenzone-3 |  | 2 | 2 | 2 | 2 | 2 | 2 | 2 | 2 | 2 | 2 |
| bis-Ethylhexyloxyphenol methoxyphenyl triazine |  | 2 | 2 | 2 | 2 | 2 | 2 | 2 | 2 | 2 | 2 |
| Ethylhexyl methoxycinnamate |  | 7 | 7 | 7 | 7 | 7 | 7 | 7 | 7 | 7 | 7 |
| Dimethicone *7 |  | 3 | 3 | 3 | 3 | 3 | 3 | 3 | 3 | 3 | 3 |
| Hydrogenated polyisobutene |  | 1.5 | 1.5 | 1.5 | 1.5 | 1.5 | 1.5 | 1.5 | 1.5 | 1.5 | 1.5 |
| EDTA-2Na•2H$_2$O |  | 0.2 | 0.2 | 0.2 | 0.2 | 0.2 | 0.2 | 0.2 | 0.2 | 0.2 | 0.2 |
| Powder | Silica K | 3 | — | — | — | — | — | — | — | — | — |
|  | Silica L | — | 3 | — | — | — | — | — | — | — | — |
|  | Silica M | — | — | 3 | — | — | — | — | — | — | — |
|  | Sericite | — | — | — | 3 | — | — | — | — | — | — |
|  | Talc A | — | — | — | — | 3 | — | — | — | — | — |
|  | Talc B | — | — | — | — | — | 3 | — | — | — | — |
|  | Talc C | — | — | — | — | — | — | 3 | — | — | — |
|  | Silicone powder A | — | — | — | — | — | — | — | 3 | — | — |
|  | Silicone powder B | — | — | — | — | — | — | — | — | 3 | — |
|  | Silicone powder C | — | — | — | — | — | — | — | — | — | 3 |
| Total |  | 100 | 100 | 100 | 100 | 100 | 100 | 100 | 100 | 100 | 100 |
| Powder properties | Shape | sphere | sphere | sphere | flake | flake | flake | flake | sphere | sphere | sphere |
|  | Avg. particle size (μm) | 9.9 | 5 | 6.3 | — | 0.85 | 1 | 7 | 0.5 | 0.8 | 5 |
|  | Oil absorption rate (mL/100 g) | 140 | <20 | 150 | — | — | — | — | — | — | — |
|  | Porous/non-porous | porous | non-porous | porous | — | — | — | — | — | — | — |
| Absorption integral value |  | 38.2 | 47.2 | 48.2 | 39.9 | 46.2 | 51.5 | 48 | 40 | 38.1 | 50.2 |
| Ultraviolet protection ability increase rate (%) |  | 97 | 120 | 122 | 101 | 117 | 131 | 122 | 102 | 97 | 127 |
| Ultraviolet protection ability increase effect |  | D | C | C | D | C | C | C | D | D | C |
| Texture |  | B | B | B | B | B | B | B | B | B | B |
| Stability (rolling test) |  | A | A | A | A | A | A | A | C | C | A |

*1 PEMULEN TR-2 (Lubrizol Advanced Materials) (Acrylates/alkyl acrylate (C10-30)) crosspolymer content: 1%)
*2 Carbopol 981 (Lubrizol Advanced Materials) (Carbomer content: 1%)
*3 Keltrol (Kelco)
*4 Emalex GWIS-160N (Nihon Emulsion)
*5 TS Polymer 50-IP (Dow Corning Toray Silicone)
*6 General formula H[OCH(CH$_3$)CH$_2$]$_n$OH (average molecular weight: approximately 1000)
*7 Silicone KF-96A-6T (Shin-etsu Chemical)

As indicated in the above Tables 1a and 1b, it was confirmed that, by blending a porous spherical powder having an average particle size of 1 to 4 μm and an oil absorption rate of 160 ml/100 g or lower, the absorbance (Abs) integral value became significantly higher, thus providing excellent ultraviolet protection ability increase effects (Examples 1 to 4).

Conversely, the increase in ultraviolet protection ability was slight in cases in which the average particle size or the oil absorption rate was not within the above-indicated ranges, or in cases in which the particle shapes were not spherical (Comparative Examples 1 to 17).

Hereinafter, an example of a formulation of the cosmetic of the present invention will be indicated. Needless to say, the present invention is not limited in any way by this formulation example, and is as defined by the claims. The blended amounts are all indicated in percentage by mass relative to the total amount of the cosmetic.

Formulation Example 1: BB Cream

| (Component name) | Blended amount (% by mass) |
|---|---|
| Purified water | balance |
| Ethanol | 8 |
| EDTA-2Na•H$_2$O | 0.05 |
| Sodium hexametaphosphate | 0.05 |
| Citric acid | 0.03 |
| Sodium citrate | 0.01 |
| (Dimethylacrylamide/sodium acryloyldimethyl taurate) copolymer | 0.3 |
| Cellulose gum | 0.2 |
| Glycerin | 2 |
| Butylene glycol | 5 |
| Polyoxyethylene (14) polyoxypropylene (7) dimethyl ether | 1 |
| Polyoxyethylene hardened castor oil (100 mol) | 1 |
| Polyoxyethylene (8 mol) behenyl ether | 1 |
| Sodium stearoylmethyl taurate | 0.1 |
| Stearyl alcohol | 0.5 |
| Behenyl alcohol | 0.5 |
| Ethylhexyl methoxycinnamate | 10 |
| Ethylhexyl triazine | 1 |
| Diethylamino hydroxybenzoyl hexyl benzoate | 1 |
| Bis-ethylhexyloxyphenol methoxyphenyl triazine | 1 |
| Isododecane | 10 |
| Caprylyl methicone | 5 |
| (Phytosteryl/octyldodecyl) N-lauroyl-L-glutamate | 0.5 |
| Dextrin (palmitate/ethylhexanoate) | 0.5 |
| Octyltriethoxysilane-treated fine-particle zinc oxide (particle size 25 nm) | 8 |
| Pigment-grade alumina-treated titanium oxide | 4 |
| Octyltriethoxysilane-treated red iron oxide | s.a. |

-continued

| (Component name) | Blended amount (% by mass) |
|---|---|
| Octyltriethoxysilane-treated yellow iron oxide | s.a. |
| Octyltriethoxysilane-treated black iron oxide | s.a. |
| Isostearic acid | 0.5 |
| Sorbitan sesquiisostearate | 0.5 |
| Fragrance | s.a. |
| Porous silica powder (average particle size 3.7 µm, oil absorption rate 120 ml/100 g) | 3 |

The invention claimed is:

1. A water-type or oil-in-water-type cosmetic containing:
(A) a porous spherical powder having an average particle size of 1 to 4 µm and an oil absorption rate of 160 ml/100 g or lower; and
(B) an ultraviolet absorption agent.

2. The water-type or oil-in-water-type cosmetic as in claim 1, wherein the (A) porous spherical powder is perfectly spherical.

3. The water-type or oil-in-water-type cosmetic as in claim 1, wherein the (A) porous spherical powder comprises silica.

4. The water-type or oil-in-water-type cosmetic as in claim 1, wherein a blended amount of the (A) porous spherical powder is 1% to 5% by mass.

5. The water-type or oil-in-water-type cosmetic as in claim 1, wherein the (B) ultraviolet absorption agent contains one or more types of both a water-soluble ultraviolet absorption agent and an oil-soluble ultraviolet absorption agent.

6. The water-type or oil-in-water-type cosmetic as in claim 1, further containing a thickener.

7. A method for increasing an ultraviolet protection ability of a water-type or oil-in-water-type cosmetic containing (B) an ultraviolet absorption agent by blending in (A) a porous spherical powder having an average particle size of 1 to 4 µm and an oil absorption rate of 160 ml/100 g or lower.

* * * * *